US00PP17123P2

(12) United States Plant Patent
Evison et al.

(10) Patent No.: US PP17,123 P2
(45) Date of Patent: Oct. 3, 2006

(54) ***CLEMATIS* PLANT NAMED 'EVIPO006'**

(50) Latin Name: *Clematis viticella*
Varietal Denomination: Evipo006

(75) Inventors: Raymond J. Evison, St. Sampson, Guernsey (GB); Mogens N. Olesen, Fredensborg (DK)

(73) Assignee: Poulsen Roser A/S & Raymond J. Evison Ltd., Fredensborg (GB)

( * ) Notice: Subject to any disclaimer, the term of this patent is extended or adjusted under 35 U.S.C. 154(b) by 712 days.

(21) Appl. No.: 10/351,413

(22) Filed: Jan. 24, 2003

(51) Int. Cl.
*A01H 5/00* (2006.01)

(52) U.S. Cl. ..... Plt./228
(58) Field of Classification Search ..... Plt./228
See application file for complete search history.

(56) References Cited

PUBLICATIONS

GTITM UPOVROM Citation For 'Evipo006' as per GB BIL 02300325.*

* cited by examiner

*Primary Examiner*—Kent Bell

(57) ABSTRACT

A new evergreen *Clematis* cultivar which has long continuous flowering season over which it produces attractive white flowers with a hint of green and a green and purple center. This new and distinct variety has shown to be uniform and stable in the resulting generations from asexual propagation.

1 Drawing Sheet

Botanical classification: Genus: *Clematis*. Species: *viticella*.

Variety denomination: 'Evipo006'.

SUMMARY OF THE INVENTION

The present discovery constitutes a new and distinct variety of *Clematis* which was discovered in a cultivated area. The cultivar originated from a crossing of pollen parent 'EVIpure', unpatented, and an unnamed seed parent, which is unpatented. The resulting cultivar was evaluated and asexually propagated by means of vegetative cuttings in a controlled environment. The new variety is named 'Evipo006'.

The claimed plant may be distinguished from the pollen parent 'EVIpure' by the following characteristics:

1. Whereas 'EVIpure' has tepals which are White Group 155C, the claimed plant has tepals which are White Group 157D.
2. Whereas 'EVIpure' has a flower diameter of 120 mm, the claimed plant has an average flower diameter of 90 mm.

The objective of the hybridization of this *Clematis* variety for commercial nursery culture was to create a new and distinct variety with unique qualities, such as:

1. Very long flowering season;
2. Evergreen if protected from frost;
3. Good flower longevity;
4. Continuous flowering period, from May to October.
5. Attractive, domed, green and purple center.

This combination of qualities was lacking in *Clematis* varieties, known to us, that were in commercial cultivation and the qualities have been substantially achieved in the new variety.

'Evipo006' was selected by Raymond J. Evison and Mogens N. Olesen in their *Clematis* development program in Domarie Vineries Les Sauvagees, St. Sampsons, Guernsey, Channel Islands, United Kingdom in June, 1996. Asexual reproduction of 'Evipo006' by cuttings was first done by Raymond J. Evison in Domarie Vineries Les Sauvagees, St. Sampsons, Guernsey, Channel Islands, United Kingdom in July, 1997. This initial and subsequent propagations have demonstrated that the characteristics of 'Evipo006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers and leaves of the new variety, with different flowers shown in various stages of maturity. The flower form, flower colors, flower buds, floral parts, flower pedicels and the cultivar's foliage are depicted. Specifically illustrated in SHEET 1:

1. Stem with attached leaves;
2. An open bloom, upper side;
3. An open bloom, lower side;
4. Stem with attached leaves and leaflets;
5. Stem with attached leaves and reproductive organs.

DETAILED DESCRIPTION OF THE VARIETY

The following is a detailed description of 'Evipo006', as observed in its growth throughout the flowering period in glasshouses at Domarie Vineries Les Sauvagees, St. Sampsons, Guernsey, Channel Islands, United Kingdom. The examination was conducted on plants which were grown for 2 years in an unheated greenhouse, in 2 liter pots. Certain phenotypical characteristics of the variety may vary under different environmental, cultural, agronomic, seasonal, and climatic conditions. Color references are made using The Royal Horticultural Society (London, England)

Colour Chart, 1995, except where common terms of color are used. For a comparison, the nearest existing *Clematis* variety is 'EVIrida', described and illustrated in U.S. Plant Pat. No. 15,093, is used. Chart 1 details the physical characteristics of 'Evipo006' and the comparison variety 'EVIrida'.

CHART 1

| | 'Evipo006' | 'EVIrida' |
|---|---|---|
| Flower Center | Inner 'ruff' of purple petaloid stamens. | Central domed location of sterile styles. |
| Flower Shape | Pom-pom shaped dome. | Flat. |
| Longevity as Cut Flower | Long Lived | Short Lived |

Parents: Unnamed Plant×'EVIpure'.

FLOWER AND FLOWER BUD

Blooming habit: Continuous.

Flower bud:

*Size.*—20–30 mm in length, 10 to 12 mm diameter.

*Bud form.*—Broad based pointed ovoid.

*Bud color.*—Yellow-Green Group 145B at ¼ open.

*Juvenile tepals.*—Yellow-Green Group 149D.

*Peduncle.*—Surface: Smooth. Light pubescence observed. Length: 90–120 mm average length. Color: Medium green. Green Group 143C. Strength: Mature peduncles have moderate strength.

*Borne.*—In compound cyme clusters.

Flower bloom:

*Size.*—Medium. 90 mm diameter on average. 25 to 30 mm in depth.

*Form.*—Upon opening, petaloid stamens form a central, densely populated whorl, normally 25 mm in diameter. At this stage of development, tepals are curved inward along a longitudinal axis, forming a pointed, elongate cone shape. Tepals flatten as flowers mature while the central whorl of petaloid stamens expands from 25 to an average 50 mm in diameter.

*Tepal color.*—Upon opening: Upper Surface: Yellow-Green Group 149D. Lower Surface: Yellow-Green Group 149D. After opening: Upper Surface: White Group 157D. Intonations of Yellow-Green Group 149D observed at the tepal apex. Lower Surface: White Group 157D, with a central streak running the length of the tepal, Yellow-Green Group 149D. The general tonality of the open flower is White Group 157D.

*Petaloid stamen color.*—On flowers which are fully open, the innermost are Yellow-Green Group 145B to 145C with apical marginal intonations of Violet Group 83A. Outermost are Violet Group 83A to Violet-Blue 92A with intonations of White Group 155C and Yellow-Green Group 145C. Base is White Group 155C.

*Fragrance.*—None.

*Lasting quality.*—28 Days on plant, 10 days as a cut flower.

Tepals:

*Tepal count.*—Single. Average range: 6 per bloom.

*Shape.*—Individual tepal shape is broad elliptical.

*Cross section.*—Flat.

*Undulation of margin.*—Weak.

*Tepal margin.*—Entire.

*Tepal apex.*—Narrowly acute to mucronate.

*Tepal base.*—Accute.

*Recurvature of tip.*—Outward recurvature develops on fully mature flowers.

*Persistence.*—Outer tepals drop off cleanly.

*Arrangement.*—Tepals are arranged regularly.

Petaloid stamens:

*Quantity.*—250 to 275 normally develop on fully open flowers.

*Shape.*—Narrow elliptic. Base is acute. Apex is acuminate.

*Recurvature.*—Innermost recurve inward. Outermost recurve outward.

*Size.*—Innermost are 8 to 10 mm long by 1 to 1.5 mm wide. Outermost are normally 25 mm long by 8 mm wide.

Reproductive organs: The claimed plant possesses incomplete reproductive parts, and is sterile.

PLANT

Plant form: Climbing and spreading.

Plant growth: Moderately vigorous.

Height: When trellised, one seasons growth attains 2.0–3.0 meters.

Spread: 1 to 2 meters.

Hardiness: Trials to date show the variety hardy in USDA zones 6–9.

Stems:

*Color.*—Young wood: Green Group 137D, with intonations of Red Purple Group N70A. Older wood: Greyed Orange Group 165C.

*Internodes.*—Cylindrical in cross section. Length 130–180 mm.

*Clasping.*—Clasps by leaf petiolus.

*Bark.*—Young wood: Smooth. Older wood: Smooth.

*Size.*—2 mm diameter. Length varies from 1 to 2 meters.

Plant foliage: Deciduous. Varies between trifoliate and pentafoliate arranged pinnately.

*Leaf size.*—Terminal leaflet of compound leaf: 40 mm in length, 25 mm wide. Simple leaf: 50 mm in length, 30 mm wide.

*Abundance.*—Average.

*Color.*—Mature Foliage Upper Side: Green Group 137A. Mature Foliage Lower Side: Green Group 137C. Juvenile Leaves Upper Side: Yellow Green 144A. Juvenile Leaves Lower Side: Yellow Green 144A.

Plant leaves and leaflets:

*Stipules.*—Absent.

*Petiole.*—Length: 30–60 mm. Underneath: Smooth. Color: Green Group 137C with intonations of Red-Purple Group 70A.

*Petioloule.*—Length is 0 to 10 mm.

*Leaf edge.*—Terminal leaflet margin is normally entire but sometimes undulated and/or with rounded lobes.

*Shape.*—Base of leaflet: Rounded. Apex of leaflet: Acute. Individual leaflet shape: Lanceolate.

*Texture.*—Thin. Upper side: Glabrous. Lower side: Ribbed.

*Surface.*—Matte Finish.

Disease resistance: Subject to any disease which normally attacks the species.

Additional information: After tepals drop off stamens fold back completely, revealing inner arrangement of sterile styles, some of which by this stage have a miniature petaloid-stamen-like appearance. This is unique. No other *Clematis* known to us displays this.

It is claimed:

1. A new and distinct variety of *Clematis* plant, known to us, substantially as herein illustrated and described, as a distinct and novel *Clematis* variety due to its abundant light green flowers, with a light green and purple center, excellent flower longevity, long recurrent flowering period from early summer through autumn, and compact growth making it suitable for nursery production in containers.

* * * * *

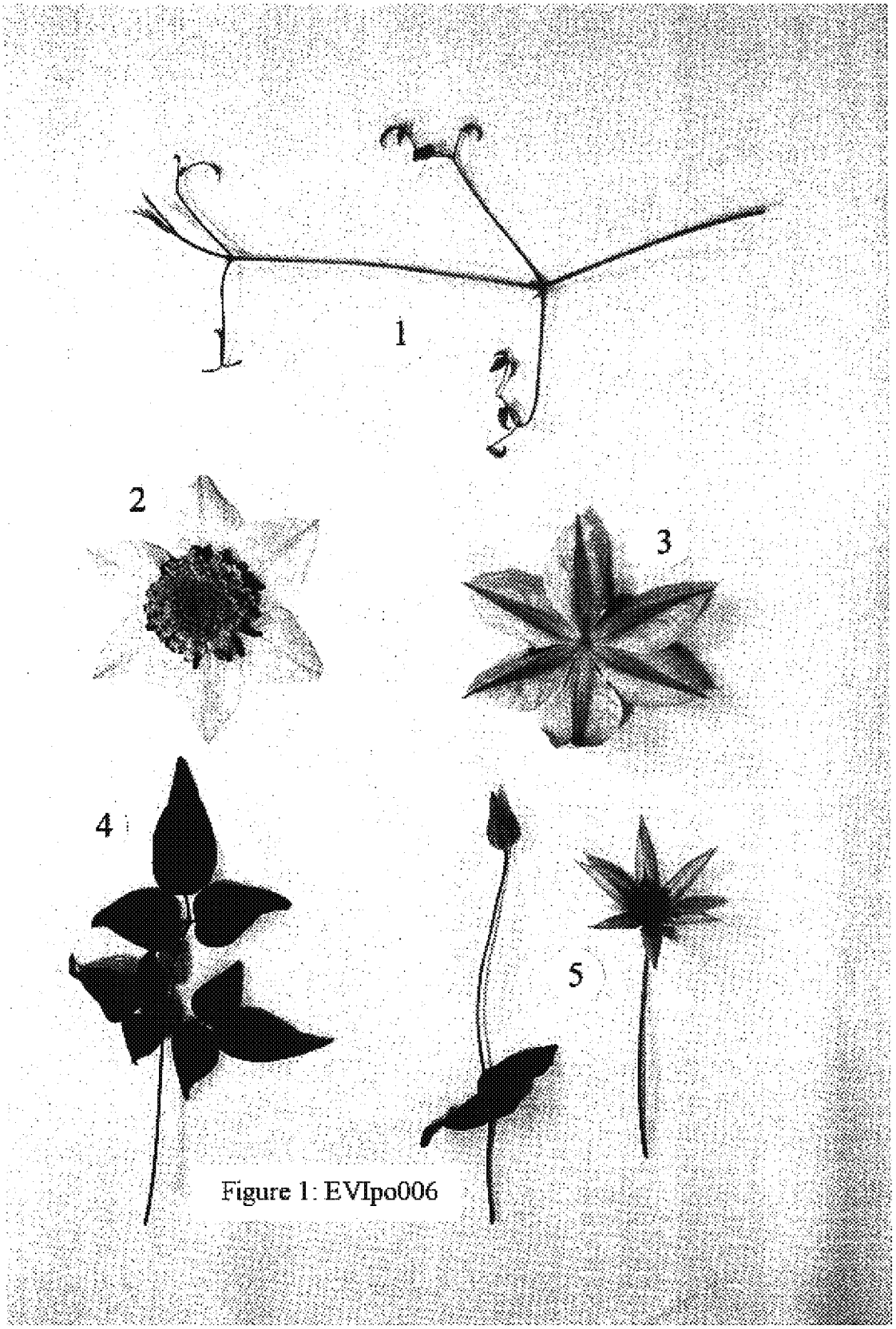
Figure 1: EVIpo006